United States Patent
Devaux

(10) Patent No.: US 6,544,936 B2
(45) Date of Patent: Apr. 8, 2003

(54) PROCESS FOR MANUFACTURING SULPHURIZED OLEFINS

(75) Inventor: Jean-Francois Devaux, Jurancon (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/840,966

(22) Filed: Apr. 25, 2001

(65) Prior Publication Data

US 2002/0016268 A1 Feb. 7, 2002

(30) Foreign Application Priority Data

Apr. 28, 2000 (FR) .............................. 00 05499

(51) Int. Cl.[7] ..................... C10M 135/02; C07C 319/04
(52) U.S. Cl. ....................... 508/324; 508/201; 508/207; 568/18; 568/59; 568/72
(58) Field of Search .......................... 508/324

(56) References Cited

U.S. PATENT DOCUMENTS

| | | | | |
|---|---|---|---|---|
| 4,102,931 A | * | 7/1978 | Buchholz ................. | 260/609 B |
| 4,119,549 A | | 10/1978 | Davis et al. ................. | 508/324 |
| 4,119,550 A | | 10/1978 | Davis ......................... | 508/324 |
| 4,191,659 A | | 3/1980 | Davis ......................... | 508/324 |
| 4,281,202 A | * | 7/1981 | Buchholz et al. ............. | 566/62 |
| 4,582,939 A | | 4/1986 | Perozzi et al. ................ | 568/72 |
| 4,584,113 A | | 4/1986 | Walsh ......................... | 508/331 |
| 4,891,445 A | | 1/1990 | Arretz ......................... | 568/72 |
| 5,091,112 A | | 2/1992 | Perozzi et al. ............... | 252/387 |
| 5,155,275 A | | 10/1992 | Shaw ......................... | 568/21 |
| 5,174,922 A | | 12/1992 | Perozzi et al. ............... | 252/395 |
| 5,206,439 A | | 4/1993 | Shaw ......................... | 568/21 |
| 5,208,382 A | | 5/1993 | Perozzi et al. ................ | 568/22 |
| 5,218,147 A | | 6/1993 | Shaw ......................... | 568/21 |
| 5,242,613 A | | 9/1993 | Ozbalik et al. ............. | 508/324 |
| 5,250,737 A | | 10/1993 | Ozbalik ....................... | 568/21 |
| 5,338,468 A | | 8/1994 | Arvizzigno et al. ........ | 508/570 |
| 5,403,961 A | | 4/1995 | Shaw ......................... | 568/21 |
| 5,457,234 A | | 10/1995 | Shaw ......................... | 568/21 |
| 5,530,163 A | | 6/1996 | Shaw ......................... | 568/26 |
| 5,559,271 A | | 9/1996 | Shaw et al. ................... | 568/21 |

FOREIGN PATENT DOCUMENTS

| | | |
|---|---|---|
| EP | 0 076 376 | 4/1983 |
| EP | 0 201 197 A1 | 11/1986 |
| EP | 0 342 454 A1 | 11/1989 |
| EP | 0 554 011 A2 | 8/1993 |
| EP | 0 656 414 | 6/1995 |
| EP | 0 714 970 A1 | 6/1996 |
| EP | 0 714 971 A1 | 6/1996 |
| EP | 0 889 030 A1 | 1/1999 |
| EP | 0 933 358 A1 | 8/1999 |
| FR | 2 607 496 | 6/1988 |
| FR | 2 630 104 | 10/1989 |
| FR | 2 757 534 | 6/1998 |
| JP | 58-140063 | 8/1983 |
| JP | 61-183392 | 8/1986 |
| JP | 11-246518 | 9/1999 |
| WO | WO 92/00367 | 1/1992 |
| WO | WO 92/03524 | 3/1992 |
| WO | WO 97/24416 | 7/1997 |

OTHER PUBLICATIONS

French Search Report for corresponding French Appln. No. FR 00.05499.

"Handbook of Molecular Sieves", R. Szostak, pp. 274–289; pp. 343–349.

* cited by examiner

*Primary Examiner*—Ellen M. McAvoy
(74) *Attorney, Agent, or Firm*—Smith, Gambrell & Russell, LLP

(57) ABSTRACT

To manufacture sulphurated products deriving from olefin(s) by sulphurization using sulphur and hydrogen sulphide, the reaction is carried out in the presence of a zeolite.

17 Claims, No Drawings

PROCESS FOR MANUFACTURING SULPHURIZED OLEFINS

DESCRIPTION

FIELD OF THE INVENTION

The present invention relates to the field of sulphurized olefins and its subject is more particularly a novel process for preparing pale-coloured sulphurized olefins, by sulphurization using sulphur and hydrogen sulphide.

BACKGROUND OF THE INVENTION

Sulphurized olefins are products widely used for sulphurizing catalysts, and as additives for lubricants or for elastomers. These products are essentially composed of mixtures of organic sulphides, disulphides and polysulphides.

The person skilled in the art knows of numerous processes for preparing sulphurized olefins or organic polysulphides. A first family of processes reacts a mercaptan and sulphur in the presence of a basic catalyst. These processes, described in the patents FR 2 607 496 and FR 2 630 104, for example, are costly since they require the use of mercaptans, which themselves have to be produced from olefins or alcohols.

The process described in the patent EP 342 454 for preparing dialkyl disulphides and dialkyl polysulphides from olefins is in fact a two-step process, where an $H_2S$+ olefin reaction is first carried out in the presence of a solid catalyst to form a mercaptan and, secondly, this mercaptan is brought into contact with sulphur and with another heterogeneous catalyst to form a polysulphide. This process has the disadvantage of requiring two steps in succession (2 different reactors) with elevated temperatures.

Other processes which can give sulphurized olefins have been proposed:

1) The olefin+sulphur reaction in the absence of $H_2S$ generally produces coloured products. To avoid this disadvantage it has been proposed to work the process in the presence of water or to carry out water washing, but this creates problems in the separation of the aqueous phase and the disposal of aqueous effluents. Processes of this type are described in the patents U.S. Pat. No. 5,338,468, WO 92/03524, WO 92/00367, WO 97/24416, EP 714 970, EP 714 971 and FR 2 757 534. In all these processes, elevated temperatures are required for good conduct of the reaction. The patent EP 201 197 describes the sulphur+olefin reaction at a temperature of from 140 to 180° C.

2) The olefin+sulphur+$H_2S$ reaction has been described. The absence of catalyst, as in the patent U.S. Pat. No. 4,119,550, forces the use of very high temperatures and pressures. The patents EP 889 030, U.S. Pat. No. 4,119,549, U.S. Pat. No. 4,191,659, U.S. Pat. No. 4,584,113 and JP 11-246518 describe this reaction with a homogeneous catalyst, which is difficult to remove at the end of the reaction. The patent EP 554 011 describes this same reaction in the presence particularly of heterogeneous catalysts which have moderate efficacy in terms of conversion at 110° C.

DESCRIPTION OF THE INVENTION

A novel process has now been found for preparing sulphurized olefins by sulphurization using sulphur and $H_2S$, giving clear, pale-coloured products and allowing the reaction to be realized in a single step.

The process according to the invention is characterized in that the reaction is carried out in a single step in the presence of a zeolite with a medium or large pore size (from 0.5 to 0.8 nm).

The zeolite to be used according to the invention is an aluminosilicate characterized by a large specific surface area and a specific pore size. The general chemical formula is $M_{2/n}O.Al_2O_3.ySiO_2.wH_2O$, where M is the cation, n is its valency, w is the amount of water of crystallization and y is greater than or equal to 2. The zeolite may be exchanged with alkali metal cations, such as $Na^+$, $Li^+$, $K^+$ or $Cs^+$, or alkaline earth metal cations, such as $Mg^{2+}$ or $Ca^{2+}$, or metal cations, such as $Ag^+$, $Co^{2+}$, $Ni^{2+}$, $Mo^{2+ \; or \; 3+}$, $Fe^{2+ \; or \; 3+}$, $Cr^{3+}$, $La^{3+}$ etc. It may also be exchanged with ammonium ions or with the H+ ion.

Although many factors can affect the catalytic activity of these zeolites, the three most important are: the structure of the skeleton and its pore size, the silica/alumina ratio in the skeleton and the nature of the cations. The zeolites according to the invention are zeolites with a medium or large pore size, in the range from 0.5 to 0.8 nm. These zeolites are preferably of type X, Y, L or mordenite, and more preferably of type Y. These zeolites are described in the *Handbook of Molecular Sieves*, R. Szostak, Van Nostrand and Reinhold, New York 1992. For example, the type X fundamental unit in the hydrated state typically has a chemical composition of $Na_{86}.[(AlO_2)_{86}.(SiO_2)_{106}].264 \; H_2O$ with pores of diameter 0.74 nm; the type Y fundamental unit in the hydrated state typically has a chemical composition of $Na_{56}.[(AlO_2)_{56}.(SiO_2)_{136}].264H_2O$ with pores of diameter 0.74 nm; the type L fundamental unit in the hydrated state typically has a chemical composition of $K_9.[(AlO_2)_9.(SiO_2)_{27}].22H_2O$ with pores of diameter 0.71 nm, and the fundamental mordenite unit in the hydrated state typically has a chemical composition of $Na_8.[(AlO_2)_8.(SiO_2)_{40}].24H_2O$ with larger-diameter 0.7 nm pores.

The initial cation coming from the synthesis may be exchanged totally or partially with alkali metal cations, alkaline earth metal cations, metal cations, ammonium or protons.

The olefins to be used in the process according to the invention may be chosen from a wide range. They contain at least one nonaromatic carbon-carbon double bond. They may generally be represented by the formula:

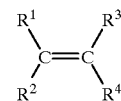

in which each of the symbols for $R^1$, $R^2$, $R^3$ and $R^4$, which are identical or different, represents a hydrogen atom, an aryl radical or an alkyl radical, linear, branched or cyclic, which contains from 1 to 20 carbon atoms and may contain one or more unsaturations and/or aromatic groups and/or $OR^5$, $SR^5$, $NR^5R^6$, CN, $COR^5$, $COOR^5$, $CONR^5R^6$, $SiR^5R^6R^7$, $Si(OR^5)R^6R^7$, $Si(OR^5)(OR^6)R^7$, $Si(OR^5)(OR^6)OR^7$, $SO_2R^5$, $SO_3R^5$, $POR^5R^6$, $OP(O)(OR^5)(OR^6)$, $NO_2$ or halogen groups, each of the symbols for $R^5$, $R^6$ and $R^7$ denoting independently a hydrogen atom or an alkyl, cycloalkyl or aryl radical optionally containing one or more unsaturations.

Two of the symbols for $R^1$, $R^2$, $R^3$ and $R^4$ may also represent an unsubstituted or substituted alkylene group: that is to say that the double carbon-carbon bond may be included in a ring, for example in cyclohexene, cyclopentadiene, dicyclopentadiene, etc. The olefin of the invention may equally be an unsaturated or polyunsaturated fatty acid, an ester of an unsaturated or polyunsaturated fatty acid, a derivative of a fatty acid containing at least one double bond, or a mixture of the latter. For example, it may be oleic acid, linoleic acid, linolenic acid, palmitoleic acid, or their esters of natural origin such as triglycerides or of synthetic origin such as, for example, esters of aliphatic alcohols or polyols. These fatty acids and esters may be used alone or mixed such as in natural fats, oils or fats of vegetable or animal origin, and derivatives thereof. Examples are sunflower oil, soybean oil, colza oil, rice bran oil, castor oil, tallow oil, tall oil, and the like. In the frame of the invention, the natural fats or their derivatives may contain some proportion of saturated acids or esters which act like solvents under the operating conditions of the invention.

The olefin of the invention may equally be a terpene, such as pinene, menthene, limonene, etc.

Mixtures of a number of olefins may also be used. By way of example, mention may be made of the mixture of a natural fat with an unfunctionallized aliphatic olefin.

It is preferable to use an olefin such as isobutylene, diisobutylene, triisobutylene, tripropylene, tetrapropylene, a fatty acid, a fatty ester, a mixture of fatty acids or esters, or an oil of vegetable or animal origin possibly mixed with an unfunctionallized aliphatic olefin.

The olefins used according to the invention may also be diluted in solvents. At the end of the reaction these solvents are vented or are separated by distillation. Examples of solvents of this type are saturated aliphatic hydrocarbons, such as methane, ethane, propane, a butane or a pentane. Using mixtures of this type made from olefins and from saturated hydrocarbons can substantially improve the cost-effectiveness of the process of the invention, since starting materials of this type can be less costly than a relatively pure olefin as starting material. For example, instead of pure isobutylene, a cut could be used comprising saturated and unsaturated hydrocarbons containing 4 carbon atoms.

Sulphur may be used in solid form, as a pellet, as a powder or in liquid form. The sulphur/olefin molar ratio may be from 0.4:1 to 2.5:1, and is preferably between 0.5:1 and 2:1.

The $H_2S$/olefin molar ratio may vary over a wide range (from 0.5:1 to 5:1, or even more), but it is preferable to use the least amount of $H_2S$ required for satisfactory working of the reaction, or an $H_2S$/olefin ratio of between 0.5:1 and 2:1.

The process according to the invention may be operated batchwise or continuously.

The catalytic efficacy of the zeolite generally becomes apparent from a minimum amount of 0.5% by weight with respect to the amount of olefin. In most cases, the maximum useful amount is of the order of 50% by weight. In a batch process the preferred amount is between 5 and 30%.

In the case of continuous operation of the process, one charge of catalyst may be used for long periods to prepare large amounts of product, and the catalyst/olefin ratio by weight is no longer of great significance.

The process according to the invention may be operated in any appropriate equipment, for example in a reactor equipped with a stirrer, where the catalyst is in suspension in the liquid reaction medium. It may also be operated using a tubular reactor, in which the catalyst is arranged in a fixed bed, in a moving bed or in an expanded bed. It is preferable to use a fixed bed reactor.

The reaction itself may take place within a wide range of temperatures, according with the olefins used and the catalyst employed. It is generally carried out at a temperature of between 20 and 180° C., preferably between 70 and 150° C.

The reaction is conducted at a pressure appropriate to the conversion of the olefin. It is advantageously worked at between 1 and 50 bar absolute, preferably between 1 and 20 bar absolute. The pressure may vary during the course of the reaction, particularly as a function of the temperature profile and of the progress of the reaction.

After a phase under pressure in a closed reactor where the olefin is converted, it is advantageous for the reactor head space to be set to atmospheric pressure or subatmospheric pressure in order to remove excess $H_2S$ and to complete the conversion of the mercaptan formed. In this latter phase it is possible to introduce an inert gas (such as methane, air or nitrogen) in order to entrain residual volatiles, such as $H_2S$, or residual olefin.

In the case of a batchwise reaction, at the end of the reaction the catalyst may be reclaimed by simple filtration and reused.

If it is desired to reduce the odour of the product, or to stabilize the same or reduce its corrosivity, the sulphurated product may be treated by any method known to the person skilled in the art. Methods of this type are described in patents JP 58-140063, U.S. Pat. No. 5,155,275, U.S. Pat. No. 5,206,439, U.S. Pat. No. 5,218,147, U.S. Pat. No. 5,403,961, U.S. Pat. No. 5,457,234, U.S. Pat. No. 5,530,163, U.S. Pat. No. 5,559,271, U.S. Pat. No. 5,091,112, U.S. Pat. No. 5,174,922, U.S. Pat. No. 5,208,382, U.S. Pat. No. 5,242,613, EP 76376 and EP 933 358, for example.

EXAMPLES

The following non-limiting examples illustrate the invention.

Example 1

60 g of extrudates of LZY-52 zeolite (marketed by UOP), an exchanged zeolite of Y type typically containing 10.4% of sodium oxide, 0.3% of calcium oxide, 0.2% of ironIII oxide, 66.5% of silica and 20.8% of alumina, and having a porosity of 0.74 nm and a specific surface area of about 820 $m^2/g$, were introduced into a 1 liter stainless-steel reactor rendered inert with nitrogen. 153 g of sulphur (4.8 mol) and 336 g of diisobutylene (3.0 mol) were then introduced. 82 g of $H_2S$ (2.4 mol) were then added over a period of 40 minutes at 20° C. The temperature was brought to 88° C. and the mixture was allowed to react for 7 hours, then for 4 additional hours. The maximum pressure achieved was 17.5 bar absolute and the pressure at the end of the reaction was 10.5 bar.

Analysis of samples shows that, after 7 hours, the reaction mixture comprised 9.2% of diisobutylene and 6.5% by weight of mercaptan (with respect to a molecular weight of 146), and then after the 4 additional hours 3.6% of diisobutylene and 6.2% by weight of mercaptan.

Filtration gave 474 g of a clear yellow oil whose total sulphur content was measured as 37% by weight. No solid sulphur deposit was found either in the liquid phase or on the filter.

Example 2 (comparative)

The conditions of Example 1 were reproduced, while the catalyst used was an activated acid alumina of type 504C (150 μm) marketed by Aldrich. The mixture was allowed to react for 11 hours at 90° C. The maximum pressure achieved was 25 bar absolute, and the pressure at the end of the reaction was 23 bar.

Analysis of the reaction mixture obtained showed a content of 34% of unconverted diisobutylene and a content of 5.6% of mercaptan.

Filtration gave 355 g of a yellow oil, and a heavy deposit of solid sulphur was seen on the filter.

Example 3

30 g of extrudates of LZY-54 zeolite (marketed by UOP), an exchanged zeolite of Y type typically containing 10% of sodium oxide, 0.23% of ironIII oxide, 66% of silica and 21% of alumina, and having a porosity of 0.74 nm and a specific surface area of about 750 m²/g, were introduced into the reactor of Example 1. 28.4 g of sulphur (0.89 mol) and 250 g of technical methyl oleate marketed by FINA CHEMICALS and containing 55% methyl oleate (0.46 mol) were then introduced. The temperature was brought to 130° C. and hydrogen sulphide was continuously added in order to keep a pressure of 13 bar absolute in the reactor. After 9 hours under those conditions, total uptake of hydrogen sulphide was 20 g.

After 1.5 hours nitrogen-stripping at atmospheric pressure, the reaction mixture contained 4.6% methyl oleate. Filtration gave 256 g of a yellow oil. No solid sulphur deposit was found either in the liquid phase or on the filter.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

What is claimed is:

1. Process for manufacturing sulphurized olefins from olefin(s), sulphur and hydrogen sulphide, comprising carrying out a reaction in a single step in the presence of a solid catalyst based on zeolite with a medium or large pore size, in the range from 0.5 to 0.8 nm.

2. Process according to claim 1, wherein the solid catalyst is a zeolite of type X, Y or L, or mordenite.

3. Process according to claim 1, wherein the solid catalyst is a zeolite of type Y.

4. Process according to claim 1, wherein the sulphur/olefin(s) molar ratio is from 0.4:1 to 2.5:1.

5. Process according to claim 1, wherein the $H_2S$/olefin(s) molar ratio is from 0.5:1 to 5:1.

6. Process according to claim 1, wherein the amount of catalyst used is from 0.5 to 50% by weight, with respect to the weight of olefin(s).

7. Process according to claim 1, wherein the process is worked at a temperature ranging from 20 to 180° C.

8. Process according to claim 1, wherein the process is worked at a pressure ranging from 1 to 50 bar absolute.

9. Process according to claim 1, wherein the olefin(s) are selected from those of the formula:

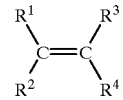

in which each of the symbols for $R^1$, $R^2$, $R^3$ and $R^4$, which are identical or different, represents a hydrogen atom, an aryl radical or an alkyl radical, linear, branched or cyclic, which contains from 1 to 20 carbon atoms and optionally contain at least one unsaturation and/or aromatic group and/or $OR^5$, $SR^5$, $NR^5R^6$, $CN$, $COR^5$, $COOR^5$, $CONR^5R^6$, $SiR^5R^6R^7$, $Si(OR^5)R^6R^7$, $Si(OR^5)(OR^6)R^7$, $Si(OR^5)(OR^6)OR^7$, $SO_2R^5$, $SO_3R^5$, $POR^5R^6$, $OP(O)(OR^5)(OR^6)$, $NO_2$ or halogen group, each of the symbols for $R^5$, $R^6$ and $R^7$ denoting independently a hydrogen atom or an alkyl, cycloalkyl or aryl radical optionally containing at least one unsaturation, and two of the symbols for $R^1$, $R^2$, $R^3$ and $R^4$ optionally also represent an unsubstituted or substituted alkylene group.

10. Process according to claim 9, wherein the olefins(s) are selected from the group consisting of isobutylene, diisobutylene, triisobutylene, tripropylene or tetrapropylene.

11. Process according to claim 9, wherein the olefin(s) are selected from the group consisting of a fatty acid, a fatty ester, a mixture of fatty acids or esters, or an oil of animal or vegetable origin.

12. Process according to claim 9, wherein the olefin(s) are selected from the group consisting of a mixture of an unfunctionalized aliphatic olefin with a fatty acid, a fatty ester or an oil of animal or vegetable origin.

13. Process according to claim 4, wherein the molar ratio is between 0.5:1 and 2:1.

14. Process according to claim 5, wherein the molar ratio is between 0.5:1 and 2:1.

15. Process according to claim 6, wherein the amount of catalyst is between 5 and 30%.

16. Process according to claim 7, wherein the temperature is between 70 and 150° C.

17. Process according to claim 8, wherein the pressure is between 1 and 20 bar absolute.

* * * * *